United States Patent [19]

Anderson et al.

[11] 4,344,030
[45] Aug. 10, 1982

[54] REMOTE DETECTOR OF FLAWS IN SURFACES USING MICRO-WAVES

[75] Inventors: Alan P. Anderson, Sheffield; John C. Jackson, Newark Notts, both of England

[73] Assignee: Lambda Industrial Science Limited, England

[21] Appl. No.: 113,970

[22] Filed: Jan. 21, 1980

[30] Foreign Application Priority Data

Jan. 20, 1979 [GB] United Kingdom ................ 7902132

[51] Int. Cl.$^3$ ............................................. G01R 27/04
[52] U.S. Cl. ................................................. 324/58.5 B
[58] Field of Search ......................... 324/58.5 B, 58 B; 73/104, 629

[56] References Cited

U.S. PATENT DOCUMENTS

| | | | |
|---|---|---|---|
| 2,999,982 | 9/1961 | Broussaud | 324/58.5 B |
| 3,144,601 | 8/1964 | Slabodsky | 324/58.5 B |
| 3,562,642 | 2/1971 | Hochschild | 324/58.5 B |
| 3,710,243 | 1/1973 | Keenan | 324/58.5 B |
| 3,936,736 | 2/1976 | Ray | 324/58.5 B X |
| 4,123,703 | 10/1978 | Robinson | 324/58.5 B |

FOREIGN PATENT DOCUMENTS 2815793  9/1979  Fed. Rep. of Germany ... 324/58.5 B

OTHER PUBLICATIONS

Hruby et al., A Novel Nondestructive, Noncontacting Method of Measuring the Depth of Thin Slits & Cracks in Metals, *The Review of Scientific Instruments*, May 1970.

Feinstein et al., A Noncontacting Device for Detection of Cracks on Metal Surfaces, *The Procedures of the 10th Symposium on NDE*, Apr. 1975.

*Primary Examiner*—Stanley T. Krawczewicz
*Attorney, Agent, or Firm*—Lowe, King, Price & Becker

[57] ABSTRACT

The invention relates to non-destructive testing for flaws in the surfaces of, particularly, billets, strip or sheet. There have been many systems developed for the detection of flaws in the surface of a workpiece such as visual techniques employing ferromagnetic materials in a fine suspension including an ultra violet dye, and techniques employing the eddy current effect, both of which suffer in that they are unsatisfactory when a workpiece is moving or when a workpiece is hot. Attempts have been made to employ micro-waves but such attempts have essentially required a very close spacing between the detector-receiver and the surface being scanned again making such equipment unsuitable for use with a moving workpiece or when a workpiece is hot. The invention overcomes these problems by providing equipment comprising a source of plane-polarized micro-wave radiation adapted for direction at a surface to be scanned, and detection means for plane-polarized micro-wave radiation reflected from the surface, the polarization directions of the transmitter and the receiver being perpendicular to each other.

8 Claims, 5 Drawing Figures

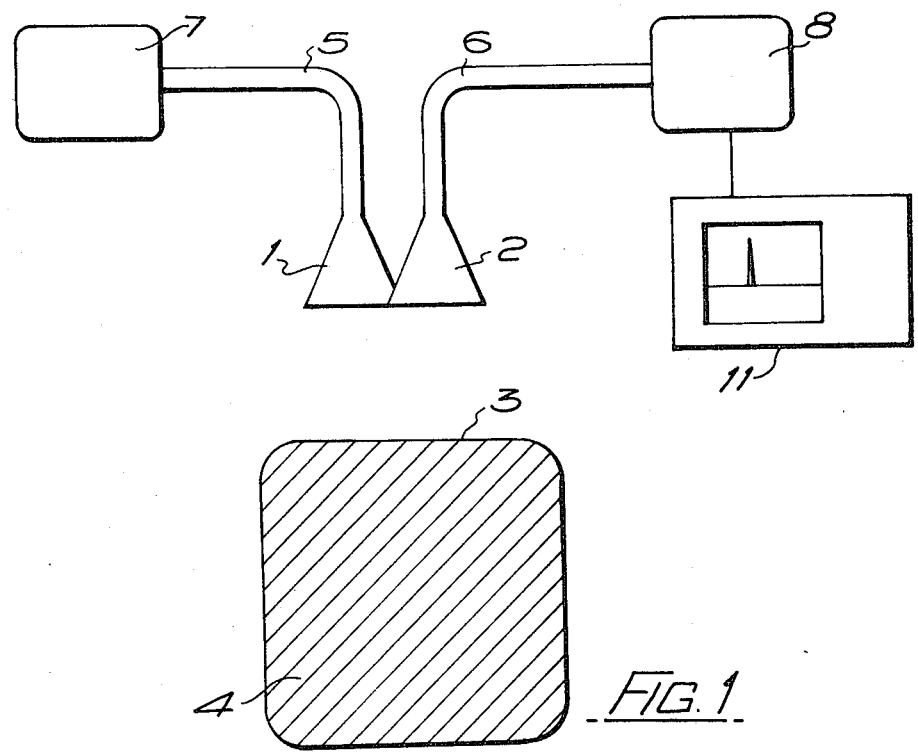
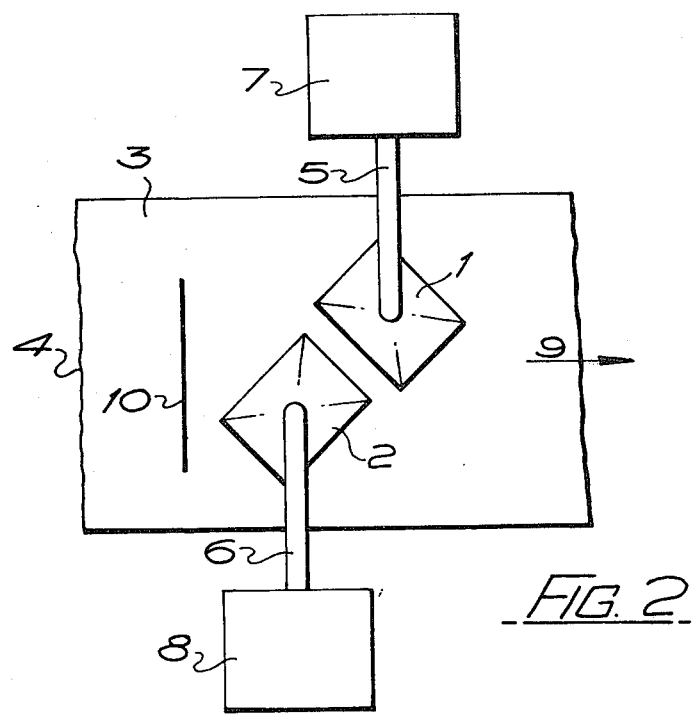

REMOTE DETECTOR OF FLAWS IN SURFACES USING MICRO-WAVES

This invention relates to the non-destructive testing for flaws, and is particularly, though non necessarily exclusively, concerned with the detection of surface flaws in billets, strip or sheet moving passed a detection point.

The presence of surface flaws such as cracks in billets, strip or sheet metal is extremely detrimental to further processing such as forging and stamping, and it is most important that such flaws are detected and removed, e.g., by grinding, before such further processing is effected. Particularly in continuous processes where the work can be moving at several feet per second, much of the inspection presently carried out is purely visual, and this is not sufficiently reliable. In an attempt to enhance visual inspection it is known with ferromagnetic materials such as steel to temporarily magnetise the material and immerse it in a suspension of fine ferromagnetic particles and an ultra violet dye. Magnetic flux leakage from the crack, with consequent enhancement of flux gradient at its sharp edges, causes the fine particles to adhere to the vicinity of the crack. Fluorescent dye is carried by the particles, and with ultra violet illumination the defect is made visible. Costly engineering installations are required to effect such techniques, so that their application is by no means universal within the ferrous metal industry. A second unsatisfactory feature of such techniques is that they do not readily lend themselves to automation. It is also the case that this technique cannot be used with hot materials.

A very effective method for the detection of cracks in stationary metallic surfaces relies upon the eddy current effect. A small coil carrying an alternating current is held close to the metal surface, typically within 1 mm. This coil induces electrical currents, known as eddy currents, just below the surface of the material. These in turn induce currents in a second small coil, held close to the metal surface and to the first coil. A crack entering the field of the first coil interfers with the flow of the induced eddy currents, and reduces their magnitude, which in turn reduces the induced currents in the receiving coil. This change is detected and indicates the presence of a crack. The major unsatisfactory feature of this technique is the need to have the coils so close to the surface, which requirement has prevented its general application to moving materials, where the motion and vibration give the surface a somewhat ill-defined location. A second unsatisfactory feature is that the technique is oversensitive in the case of ferromagnetic materials, where it can give undesired responses, for example to changes in crystal structure. For this reason the method is usually applied only to non-magnetic materials. Here again, this technique cannot be utilised with hot materials.

Attempts have been made to employ micro-waves in the field of non-destructive testing. Thus, in an article by Hruby and Feinstein in The Review of Scientific Instruments, Volume 41 number 5 of May 1970 entitled "A Novel Nondestructive, Noncontacting Method of Measuring the Depth of Thin Slits and Cracks in Metals", there is discussed a technique whereby non-polarised micro-waves are directed through an aperture against a surface, and when any slot or slit in the surface is intercepted by the non-polarised micro-waves to transform part of the scanning signal to a polarisation angle dependent signal, from which the depth of a known slot deliberately positioned below the device can be measured. In an article by Feinstein, Cysel and Robinson in The Procedures of the 10th Symposium on NDE, San Antonio, April 1975 entitled "A Noncontacting Device for Detection of Cracks on Metal Surfaces", there is the discussion of a detector making use of the capability of two coupled strip lines, wherein two conductors printed on a di-electric sheet whose other side is clad with metal scan a metal surface at a close distance such that the metal surface becomes part of the RF ground conductor. The two strip lines are excited in one mode and a crack in the metal surfaces couples energy into the other mode because the crack upsets the symmetry of the coupled lines. In both items of prior art it is clearly specified that the flaw must be spaced from the sensing head by a fraction of the wave length of the micro-waves and accordingly both disclosures are totally unsuited for use in the continuous surveillance of such items as billets, strip or sheet moving passed the detection point. The close proximity of the device to the moving surface would be such that damage would be occasioned the equipment to an extent sufficient to render such proposals totally unworkable, and they could not readily be utilised with any hot workpiece.

The object of the present invention is to provide means whereby non-destructing testing of a metal surface utilising micro-waves can be employed which would not be damaged if the workpiece and the detector were moving relative to each other.

According to the present invention, non-destructive testing means for flaw detection comprises a source of plane-polarised micro-wave radiation adapted for direction at a surface to be scanned, and detection means for plane-polarised micro-wave radiation reflected from the surface, the polarisation directions of the transmitter and the receiver being perpendicular to each other. Preferably, the transmitter and receiver are in the form of transmitting and receiving horns, although a single horn capable of both transmitting and receiving plane-polarised micro-waves and receiving plane-polarised micro-waves having a polarisation perpendicular to the transmitted waves could be used.

By directing a beam of plane-polarised micro-wave radiation against the surface and detecting plane-polarised reflection from the surface, the transmitter and receiver can be spaced by a distance away from the surface such that they will not be effected by vibration induced by movement of the scanned surface or by any irregularities in the scanned surface, or be affected by heat radiating from the surface, thereby ensuring that such means can be employed in the continuous scanning of a billet, strip or sheet moving passed a detection point.

To explain the underlying principle of the device of the invention, when a beam of plane-polarised micro-wave radiation is directed at the surface to be scanned, at approximately normal incidence, although this is not essential, the electrical field has a constant direction known as the polarisation direction. Although wave length is not critical a typical value would be 8 mm. This beam is reflected at the surface, and, if the surface is free of flaws, the polarisation plane in the reflected beam coincides with that in the incident beam. To understand how the reflected beam is affected by the presence of a crack in the surface, an understanding of the reflection process is essential. In very general terms, it may be said that radiation incident on a conducting surface causes the conduction electrons within the material close to the surface, within a distance known as the skin depth, to undergo oscillatory motion at the radiation frequency. Electrons undergoing such motion generate radiation, and it is the combination of such re-generated waves which constitutes the reflected beam.

In the case of plane-polarised incident radiation, the induced electron motions are all in the polarisation direction, that is if the surface is free of flaws. These oscillations re-generate plane-polarised waves, which combine to give a reflected beam which has the same polarisation as the incident beam. However, if the surface has a linear flaw, so that its electrical continuity is broken along a line, those electrons adjacent to the flaw are constrained to move in a direction parallel to the flaw. In this case the reflected beam contains a component which is plane-polarised in the flaw direction, which in general will not coincide with the polarisation direction of the incident beam. Hence a receiver, set up to respond only to reflected beams which are plane-polarised in a direction perpendicular to the polarisation direction of the incident beam, will give no response if the surface is free of flaws. A received signal indicates the presence of a flaw. The response of such a system depends upon the angle between the flaw direction and the incident polarisation direction, being zero if the two directions happen to coincide, and a maximum when this angle is 45°. For complete reliability, particularly if the system is to have a calibration in which the response is related to the flaw severity, the orientation of the flaws must be known. In practice this is not a serious limitation.

Two embodiments of the invention will now be described by way of example only with reference to the schemmatic drawings, in which:

FIG. 1 is an end elevation of a device in accordance with the invention for use in the detection of applications in a continuously moving workpiece;

FIG. 2 is a plan view of the device of FIG. 1;

Figure 5:
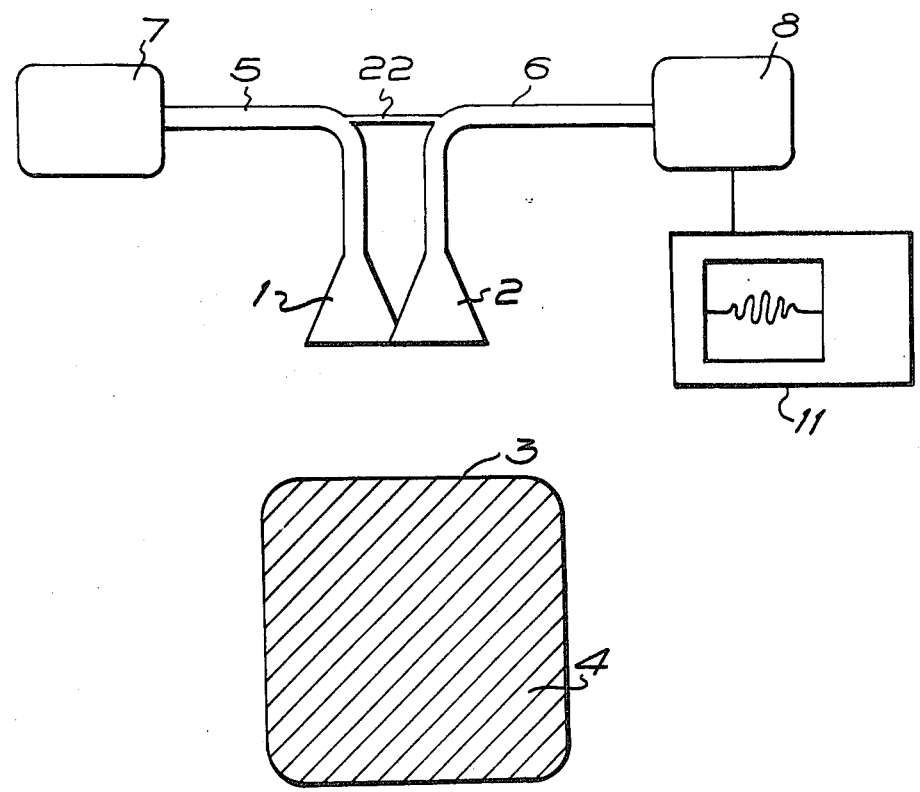

FIG. 5 corresponds to FIG. 1, but shows a further embodiment of the invention.

In FIGS. 1 and 2, there is shown a means for the detection of cracks in steel billets produced by a continuous casting process in which liquid steel enters one end of a vibrating cooled mould and emerges from the other end as a solid billet. In such process there is the generally inevitable production of surface cracks which are predominantly on the faces of the billet and perpendicular to its length. For such an application, detection means in accordance with the invention comprises transmitting and receiving horns 1 and 2 respectively fixed above face 3 of billet 4, typically 60 mm away from this face, as shown in FIG. 1. Their polarisation directions are perpendicular to each other and at 45° to the billet length. These horns are connected via waveguides 5 and 6 to micro-wave transmitter 7 and receiver 8 respectively. The transmitting horn illuminates a region on face 3 covering almost the full width of the face, which region is viewed by the receiving horn. As the billet moves along its length in direction 9 of FIG. 2, for example, as it emerges from the continuous casting machine, or at a later stage in its transportation, cracks such as 10 pass under the two horns simultaneously, and the receiver gives a corresponding series of output pulses. These can start an alarm and be recorded on an oscilloscope or chart recorder 11, or can initiate an automatic process, whereby the cracks are marked, and defective billets are diverted to an area reserved for their inspection and treatment. Four such systems would examine the four faces of the billet simultaneously.

In accordance with the invention, the expensive and delicate components of the system, namely transmitter 1 and receiver 2, can be mounted well away from the material being examined, where risk of damage is greatly reduced. The clearance between horns 1 and 2 and face 3 is sufficient to accommodate any likely variation in the location of this surface, and is also great enough to prevent undue heating of these components if the material is very hot, as it would be leaving a continuous casting machine. In any case, horns and waveguides are relatively inexpensive items, and can be treated as disposable parts of the system.

Figure 3:
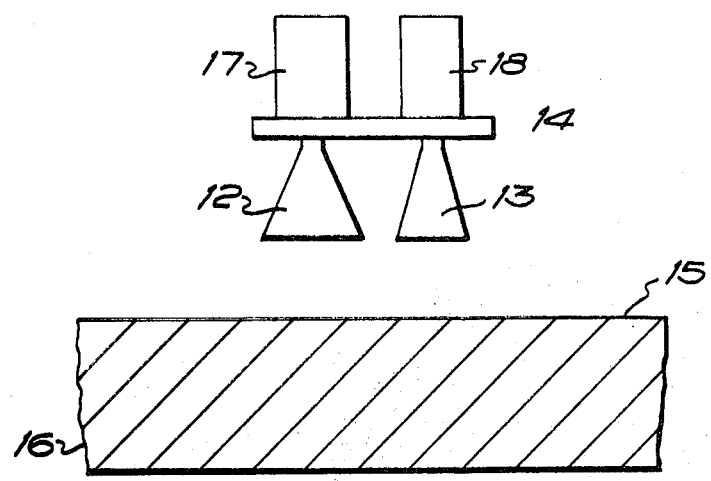
FIG. 3 is an end elevation of a device in accordance with the invention for continuous movement across a workpiece.
Figure 4:
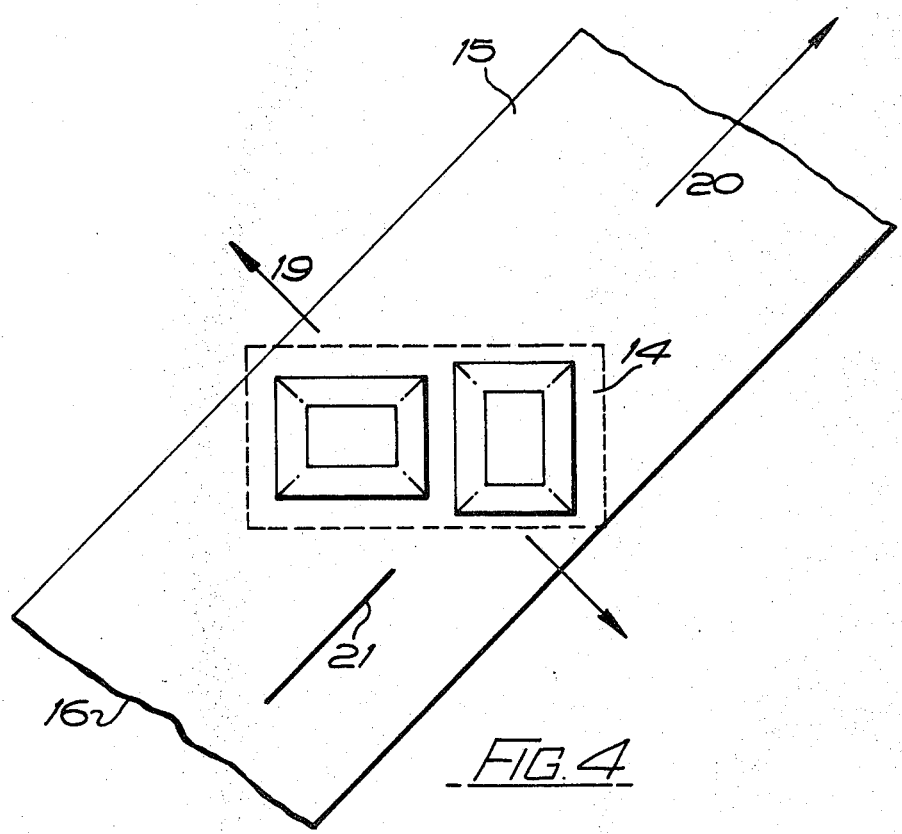
FIG. 4 is a plan view of the device of FIG. 1.

In FIGS. 3 and 4, there is shown the application of the invention to billets produced by rolling, and where billets are produced in a rolling mill where a casting ingot is heated and passed through a train of rolls where its length is elongate and its cross-section reduced. Flaws here are normally produced predominantly along the billet length and are generally somewhat longer than in continuously cast billets. To detect such flaws transmitting and receiving horns 12 and 13 mounted on a movable platform 14 are positioned above face 15 of billet 16, as shown in FIG. 3. Transmitter 17 and receiver 18 are also mounted on platform 14 and electrical connections for power and signal transmission are made via flexible cables. Components are readily available to make this movable installation small and light, so that rapid mechanical scanning is possible. Platform 14 is scanned mechanically in an oscillatory fashion in direction 19 of FIG. 4, carrying with it the transmitting and receiving components. The extent of this motion is of the order of the billet width. At any one instant the region observed by the system is approximately 10 mm in linear extent, i.e., somewhat smaller than the billet width. As the billet moves along its length in direction 20, flaws such as crack 21 pass under the system, and the receiver gives a well-defined pulse as the horns simultaneously pass over the crack, once during each scan. The characteristics of this pulse are related to the severity and nature of the flaw. To give full area coverage of a billet moving at 0.3 m/s, a scanning rate of about 30 Hz would be required. Electronic alternatives to mechanical scanning are available, for example using a linear array of stationary horns. Electronic scanning would be particularly useful for high scanning rates, and it is to be understood that the method revealed here includes the use of such techniques.

To render the device of the invention more sensitive and discriminatory, irrespective of its particular application, it is preferred as is shown in FIG. 5 to pass a reference signal directly from the transmitter to the receiver and when weak signals re-radiated by the flaws can be detected with greater accuracy. By providing a reference signal 22, there is produced the combination of the back-scattered signal with the reference signal, which gives rise to an interference pattern output from the detector as the flaw is scanned by the detector. This one dimensional holograph i.e. signature of the flaw is recognisable and provides discrimination in the presence of noise. If desired, the holographic signature may be further processed by appropriate means to provide a pulse shape output, a particularly useful feature when more than one flaw is present within the field of view of the detector giving a more complex holographic signature. Formation of the holographic signature and its further processing for output as shaped pulses are accomplished by conventional circuit means long used in the holographic arts. A typical disclosure source for such prior art application herein is the text "Theory and Applications on Holography" by Develis and Reynolds, published by Addison-Wesley, New York and London, edition of 1967. Knowledge in the prior art of obtaining and processing refined signal indications characteristic of the detected flaw, such as the aforesaid signature, by mixing the detected signals with reference signals, also appears from U.S. Pat. No. 3,144,601, granted Aug. 11, 1964, to Slabodsky, in its column 3, first paragraph. Moreover, this processed data can provide a two-dimensional image format if the micro-wave device is scanned relative to the workpiece in two orthogonal directions.

We claim:

1. A non-destructive testing means for detecting flaws in a material surface moving relative to said testing means comprising
a transmitter of plane-polarised microwave radiation directing said radiation as an incident beam for scanning said surface therewith,
a receiver of plane-polarised microwave radiation selectively detecting beamed plane-polarised microwave radiation reflected from said surface in response to said incident beam on said surface,
said transmitter and receiver in their operative arrangement having their polarisation directions disposed perpendicular to each other such that the presence and absence of said flaws are indicated by, respectively, presence and absence of detection by said receiver of beamed reflected radiation plane-polarised perpendicular to said plane-polarisation of said incident beam.

2. Non-destructive testing means for flaw detection as in claim 1, wherein the transmitter and receiver are in the form of transmitting and receiving horns.

3. Non-destructive testing means for flaw detection as in claim 1, wherein a single horn capable of both transmitting and receiving plane-polarised micro-waves and receiving plane-polarised micro-waves having a polarisation perpendicular to the transmitted waves is provided.

4. Non-destructive testing means for flaw detection as in any of claims 1, 2 and 3, wherein the polarisation directions of the transmitter and detector are at an acute angle to said flaw direction in the surface to be scanned.

5. Non-destructive testing means for flaw detection as in any of claims 1, 2 and 3, wherein the polarisation directions of the transmitter and detector are at 45° to said flaw direction in the surface to be scanned.

6. Non-destructive testing means for flaw detection as in any of claims 1 and 2 wherein a reference signal is passed directly from the transmitter to the receiver.

7. Non-destructive testing means for flaw detection as in claim 6, wherein the output from the receiver is represented as a one dimensional holographic signature.

8. Non-destructive testing means for flaw detection as in any of claims 1 and 2 wherein means are provided for the conversion of the holographic signature to a pulse shape.

* * * * *